United States Patent
Burgess et al.

(10) Patent No.: US 8,956,593 B2
(45) Date of Patent: Feb. 17, 2015

(54) ORAL CARE COMPOSITIONS WITH IMPROVED RHEOLOGY

(75) Inventors: Steven Carl Burgess, Sharonville, OH (US); Ayowumi O. Fatade, Indianapolis, OH (US)

(73) Assignee: The Procter & Gamble Co., Cincinnati, OH (US)

( * ) Notice: Subject to any disclaimer, the term of this patent is extended or adjusted under 35 U.S.C. 154(b) by 0 days.

(21) Appl. No.: 13/596,719

(22) Filed: Aug. 28, 2012
(Under 37 CFR 1.47)

(65) Prior Publication Data

US 2013/0280182 A1    Oct. 24, 2013

Related U.S. Application Data

(60) Provisional application No. 61/530,059, filed on Sep. 1, 2011.

(51) Int. Cl.
| | | |
|---|---|---|
| *A61Q 11/00* | (2006.01) | |
| *A61K 8/21* | (2006.01) | |
| *A61K 8/25* | (2006.01) | |
| *A61K 8/86* | (2006.01) | |
| *A61K 8/69* | (2006.01) | |
| *A61K 8/34* | (2006.01) | |
| *A61K 8/22* | (2006.01) | |
| *A61K 8/55* | (2006.01) | |
| *A61K 8/24* | (2006.01) | |

(52) U.S. Cl.
CPC . *A61K 8/69* (2013.01); *A61K 8/345* (2013.01); *A61Q 11/00* (2013.01); *A61K 8/86* (2013.01); *A61K 8/22* (2013.01); *A61K 8/55* (2013.01); *A61K 8/24* (2013.01); *A61K 8/25* (2013.01); *A61K 8/21* (2013.01)
USPC ............................... 424/49; 424/52; 424/401

(58) Field of Classification Search
USPC .............................................. 424/49, 52, 401
See application file for complete search history.

(56) References Cited

U.S. PATENT DOCUMENTS

| | | | |
|---|---|---|---|
| 2,946,725 A | 7/1960 | Norris et al. | |
| 3,070,510 A | 12/1962 | Cooley et al. | |
| 3,111,127 A | 11/1963 | Jarboe | |
| 3,535,421 A | 10/1970 | Briner et al. | |
| 3,538,230 A | 11/1970 | Pader | |
| 3,678,154 A | 7/1972 | Widder et al. | |
| 3,689,637 A | 9/1972 | Morton | |
| 3,703,578 A | 11/1972 | Cella et al. | |
| 3,917,613 A | 11/1975 | Humbert et al. | |
| 3,959,458 A | 5/1976 | Agricola et al. | |
| 3,991,178 A | 11/1976 | Humbert et al. | |
| 4,029,759 A | 6/1977 | Humbert et al. | |
| 4,051,234 A | 9/1977 | Gieske et al. | |
| 4,136,163 A | 1/1979 | Watson et al. | |
| 4,150,052 A | 4/1979 | Watson et al. | |
| 4,153,679 A | 5/1979 | Rowsell et al. | |
| 4,157,384 A | 6/1979 | Watson et al. | |
| 4,178,459 A | 12/1979 | Watson et al. | |
| 4,206,215 A | 6/1980 | Bailey | |
| 4,230,688 A | 10/1980 | Rowsell et al. | |
| 4,340,583 A | 7/1982 | Wason | |
| 4,459,425 A | 7/1984 | Amano et al. | |
| 4,627,977 A | 12/1986 | Gaffar et al. | |
| 4,894,220 A | 1/1990 | Nabi et al. | |
| 4,956,167 A * | 9/1990 | Aldcroft et al. ............... 423/339 |
| 5,004,597 A | 4/1991 | Majeti et al. | |
| 5,015,466 A | 5/1991 | Parran, Jr. et al. | |
| 5,180,577 A | 1/1993 | Polefka et al. | |
| 5,266,592 A | 11/1993 | Grueb | |
| 5,281,410 A | 1/1994 | Lukacovic et al. | |
| 5,451,404 A | 9/1995 | Furman | |
| 5,578,293 A | 11/1996 | Prencipe et al. | |
| 5,589,160 A | 12/1996 | Rice | |
| 5,603,920 A | 2/1997 | Rice | |
| 5,608,119 A | 3/1997 | Amano et al. | |
| 5,651,958 A | 7/1997 | Rice | |
| 5,658,553 A | 8/1997 | Rice | |
| 5,703,123 A | 12/1997 | Pelzer et al. | |
| 5,716,601 A | 2/1998 | Rice | |
| 5,725,865 A | 3/1998 | Mane et al. | |
| 5,843,466 A | 12/1998 | Mane et al. | |
| 5,977,166 A | 11/1999 | Greenberg | |
| 6,221,340 B1 * | 4/2001 | Yu et al. ............................ 424/49 |
| 6,365,215 B1 | 4/2002 | Grainger et al. | |
| 6,451,844 B1 | 9/2002 | Watkins et al. | |

(Continued)

FOREIGN PATENT DOCUMENTS

| | | |
|---|---|---|
| EP | 310299 | 4/1989 |
| GB | 1315626 | 5/1973 |

(Continued)

OTHER PUBLICATIONS

International Search Report for PCT/US2012/052654—Nov. 16, 2012.

*Primary Examiner* — Lezah Roberts

(74) *Attorney, Agent, or Firm* — Alexander S. Anoff; James E. Oehlenschlager

(57) ABSTRACT

Topical compositions containing from about 40% to about 77% by weight of the composition of a humectant component, said component containing from about 0.25% to about 7% of a structuring humectant selected from polyethylene glycols having an average molecular weight of from about 3,000 to about 8,000, and mixtures thereof; and at least one secondary humectant; the topical composition further comprises abrasive from about 5% to about 35%; from about 0% to about 1.5% of a viscosity modifier; a total solids content of 50% or less; water from about 5% to about 12%; and wherein the structuring humectant is added to the composition in solution with solvent or is added in a controlled manner as a molten material to the composition at a temperature less than about 35° C. and with turbulent mixing or vigorous agitation.

17 Claims, No Drawings

(56) References Cited

U.S. PATENT DOCUMENTS 6,592,884 B2 7/2003 Hofmann et al.
6,884,903 B2 4/2005 Lorenz
6,956,139 B2 10/2005 Green et al.
7,189,760 B2 3/2007 Erman et al.

FOREIGN PATENT DOCUMENTS

| WO | WO2005049553 | 6/2005 |
| WO | WO2006103401 | 10/2006 |
| WO | WO 2011/160996 A1 | 12/2011 |

* cited by examiner

ORAL CARE COMPOSITIONS WITH IMPROVED RHEOLOGY

CROSS REFERENCE TO RELATED APPLICATIONS

This application claims the benefit of U.S. Provisional Application No. 61/530,059, filed Sep. 1, 2011.

FIELD OF THE INVENTION

The present invention relates to topical compositions, such as oral care compositions, having improved rheology containing humectants such as polyethylene glycol.

BACKGROUND OF THE INVENTION

Traditionally, much effort has been expended to balance a number of important consumer-related factors in an oral care composition, such as a dentifrice. Because of the nature of such compositions, consumers have come to expect a variety of efficacy benefits such as cleaning, whitening, gum health, and the like. However, since the compositions are typically used in the mouth and are delivered by use of a toothbrush, additional care must be given to viscosity, rheology, mouth feel and taste as these are also important to consumers. A particular consumer concern is that a composition not be too runny or too thick but will fairly easily dispense out of a tube or other packaging and then sit on top of the toothbrush bristles. Efforts to improve these attributes are therefore common in the art, with varying success.

Cleaning abrasives such as silicas, (for example cleaning precipitated silicas) have been used in dentifrice compositions to mechanically clean the tooth surface.

Humectants such as polyethylene glycols have been used in dentifrice compositions to modify viscosity and to provide a smooth feel to dentifrice compositions. Polyethylene glycols are available in a large range of average molecular weights and have different properties depending upon their average molecular weights.

Despite the wide array of dentifrice products currently available, a need still exists for a composition that can provide good cleaning and efficacy while delivering good rheology and viscosity to improve the consumer use experience.

SUMMARY OF THE INVENTION

A topical composition is provided that comprises humectant component from about 40% to about 77% by weight of the composition, wherein the humectant component comprises from about 0.25% to about 7% by weight of the composition, of a structuring humectant selected from polyethylene glycols having an average molecular weight of from about 3,000 to about 8,000, and mixtures thereof; and at least one secondary humectant; the topical composition further comprises abrasive from about 5% to about 35% by weight of the composition; from about 0% to about 1.5% by weight of the composition, of a viscosity modifier selected from gums, binders, cellulosic thickeners, and mixtures thereof; a total solids content of 50% or less by weight of the composition; water from about 5% to about 12% by weight of the composition; and wherein the structuring humectant is added to the composition in solution with solvent or is added in a controlled manner as a molten material to the composition at a temperature less than about 35° C. and with turbulent mixing or vigorous agitation.

An oral care composition is provided that comprises humectant component from about 40% to about 77% by weight of the composition, wherein the humectant component comprises structuring humectant from about 0.25% to about 7%, by weight of the composition, selected from polyethylene glycols having an average molecular weight of from about 3,000 to about 8,000, and mixtures thereof; and at least one secondary humectant; the oral care composition further comprises fluoride from about 50 ppm to about 3500 ppm; from about 0% to about 1.5% by weight of the composition of a viscosity modifier selected from gums, binders, cellulosic thickeners, and mixtures thereof; from about 5% to about 35% by weight of the composition of an abrasive; surfactant from about 0.025% to about 9% by weight of the composition; a total solids content of 50% or less by weight of the composition; and water from about 5% to about 12% by weight of the composition; and wherein the composition comprises a water activity value of from about 0.25 to about 0.46 measured at about 22° C.; and wherein the structuring humectant is added to the composition in solution with solvent or is added in a controlled manner as a molten material to the composition at a temperature less than about 35° C. and with turbulent mixing or vigorous agitation.

DETAILED DESCRIPTION OF THE INVENTION

It has now been surprisingly found that a non-anhydrous yet low water dentifrice composition containing cleaning silicas, may be internally structured by regulating the composition's level of water activity and incorporating a structuring humectant.

Active and other ingredients useful herein may be categorized or described herein by their cosmetic and/or therapeutic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated function(s) or activities listed.

These elements will be discussed in more detail below.

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated.

All measurements referred to herein are made at 22° C. (i.e. room temperature) unless otherwise specified.

As used herein, the word "about" means +/−10 percent.

As used herein, the word "include," and its variants, are intended to be non-limiting, such that recitation of items in a list is not to the exclusion of other like items that may also be useful in the materials, compositions, devices, and methods of this invention.

These elements will be discussed in more detail below.

The compositions herein are useful for topical application. In one embodiment, the composition is an oral care composition.

As used herein, "oral care composition" is meant a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral care composition may be in various forms including toothpaste, dentifrice, tooth gel, subgingival gel, mouthrinse, mousse, foam, mouthspray, lozenge, chewable tablet, chewing gum or denture product. In one embodiment, the oral care composition is in a form selected from toothpaste, dentifrice, tooth gel, mouth rinse or denture product. The oral care composition may also be incorporated onto strips or films for direct application or attachment to oral surfaces.

The term "dentifrice", as used herein, includes paste, gel, or liquid formulations unless otherwise specified. The dentifrice can be in a dual phase form, like a striped paste for example, and can also be used as a regimen.

The term "teeth", as used herein, refers to natural teeth as well as artificial teeth or dental prosthesis and is construed to include one tooth or multiple teeth.

The compositions herein contain from about 40% to about 77%, by weight of the composition, of a humectant component. In one embodiment, the compositions herein contain from about 45% to about 67%, by weight of the composition, alternatively from about 45% to about 62% of the humectant component.

The humectant component contains a structuring humectant and at least one secondary humectant.

The composition contains from about 0.25% to about 7%, by weight of the composition, of the structuring humectant. In one embodiment, the composition contains from about 0.5% to about 4%, by weight of the composition, of the structuring humectant.

The structuring humectant is selected from polyethylene glycols having an average molecular weight of from about 3,000 to about 8,000, and mixtures thereof. In one embodiment, the structuring humectant is selected from polyethylene glycols having an average molecular weight of from about 3,000 to about 6,000, alternatively from about 3,500 to about 5,500.

Polyethylene glycol materials having an average molecular weight of from about 3,000 to about 8,000 are commercially available from such suppliers as Dow Chemical and BASF (New Jersey, USA). Examples of commercially available polyethylene glycol materials useful herein include PEG 4000 PLURIOL E 4000 Pastille and PEG 8000 PLURIOL E 8000 NF Prill having an average molecular weight of 4000 and 8000, respectively commercially available from BASF (Florham Park, N.J., USA).

Without being limited by theory, in order to ensure a structuring crystalline structure is created in the composition, the structuring humectant is added to the composition in solution with solvent (e.g., water) or is added in a controlled manner as a molten material to the composition, in certain embodiments with the temperature less than about 35° C. and with turbulent mixing or vigorous agitation.

The humectant component contains at least one secondary humectant. The secondary humectant is selected from glycerin, glycerols, sorbitol, polypropylene glycol, low molecular weight polyethylene glycols, edible polyhydric alcohols, and mixtures thereof. In one embodiment, the secondary humectant is selected from glycerin, sorbitol and low molecular weight polyethylene glycols The compositions herein may further include from about 50 ppm to about 3500 ppm of fluoride, wherein the fluoride is selected from stannous fluoride, sodium fluoride, sodium monofluorophosphate, and mixtures thereof. In one embodiment, the fluoride is selected from sodium fluoride, stannous fluoride, and mixtures thereof, in another embodiment the fluoride is stannous fluoride.

In one embodiment, the composition contains from about 650 ppm to about 1500 ppm, alternatively from about 900 ppm to about 1300 ppm of fluoride.

In one embodiment, the fluoride is present in the oral care composition in an amount sufficient to give a fluoride ion concentration in the composition of from about 0.0025% to about 5.0% by weight to provide anticaries effectiveness. In one embodiment, the fluoride concentration is from about 0.005% to about 2.0% by weight. A wide variety of fluoride ion-yielding materials can be employed as sources of soluble fluoride in the present compositions and methods. Examples of suitable fluoride ion-yielding materials are found in U.S. Pat. No. 3,535,421 to Briner et al. and U.S. Pat. No. 3,678,154 to Widder et al. Representative fluoride ion sources include: stannous fluoride, sodium fluoride, potassium fluoride, amine fluoride, sodium monofluorophosphate, indium fluoride, amine fluorides such as Olaflur, and mixtures thereof.

The compositions herein may contain from about 0% to about 1.5%, by weight of the composition, of a viscosity modifier selected from gums, binders, cellulosic thickeners, and mixtures thereof.

The compositions herein may contain from about 5% to about 35%, by weight of the composition, of an abrasive. In one embodiment, the abrasive is selected from fused silica, precipitated silica, and mixtures thereof. In one embodiment, the composition contains from about 10% to about 35%, alternatively from about 15% to about 35%, alternatively from about 15% to about 30%, by weight of the composition, of the abrasive.

In one embodiment, the abrasive is a precipitated silica. In one embodiment, the abrasive is precipitated silica having an oil absorption of less than about 250 cc/100 g, a BET surface area of less than about 150 m2/g, and a median particle size of less than about 50 microns. In another embodiment, the precipitated silica has a particle size of from about 5 to about 20 microns. Abrasive precipitated silicas are commercially available from Huber under the tradename ZEODENT (Havre de Grace, Md., USA).

Additional abrasives such as fumed silica, pumice, bioactive glass, and mixtures thereof may also be used in small amounts. The abrasive contemplated for use in the compositions of the present invention can be any material that does not excessively abrade dentin. Typical abrasives include silicas including gels and precipitates; aluminas; phosphates including orthophosphates, polymetaphosphates, and pyrophosphates; and mixtures thereof. Specific examples include dicalcium orthophosphate dihydrate, calcium pyrophosphate, tricalcium phosphate, calcium polymetaphosphate, insoluble sodium polymetaphosphate, hydrated alumina, beta calcium pyrophosphate, calcium carbonate, and resinous abrasive materials such as particulate condensation products of urea and formaldehyde, and others such as disclosed by Cooley et al in U.S. Pat. No. 3,070,510, issued Dec. 25, 1962. In one embodiment, the dentifrice comprises a polyphosphate having an average chain length of about 4 or more and is substantially free of calcium-containing abrasives and alumina.

In certain embodiments, the composition comprises less than 5%, by weight of the composition, of silica gels. In one embodiment, the composition comprises less than about 5%, by weight of the composition, of a thickening silica, alternatively less than about 2%, alternatively less than 1%, by weight of the composition, of a thickening silica.

Silica gels include, for example, the silica xerogels described in Pader et al., U.S. Pat. No. 3,538,230, issued Mar. 2, 1970. Silica gels are commercially available and marketed under the trade name SYLOID by the W.R. Grace & Company, Davison Chemical Division.

Without being limited by theory, it is believed that the low water compositions herein enable the use of a single abrasive in addition to allowing for the use of smaller amounts of abrasives in combination with precipitated and/or fused silica.

In certain embodiments, the abrasive is a silica having an average particle size ranging between about 0.1 to about 30 microns, and preferably from about 5 to about 15 microns. Types of silica dental abrasives useful in the toothpastes of the present invention are described in more detail in Wason, U.S. Pat. No. 4,340,583, issued Jul. 29, 1982. Silica abrasives are also described in Rice, U.S. Pat. Nos. 5,589,160; 5,603,920; 5,651,958; 5,658,553; and 5,716,601. In one embodiment, the abrasive in the toothpaste compositions described herein is present at a level of from about 6% to about 70% by weight of the composition.

The present invention may include a polymeric anti-tartar, anti-stain agent. A polymeric anti-tartar, anti-stain agent may be a polyphosphate. A polyphosphate is generally understood to consist of two or more phosphate molecules arranged primarily in a linear configuration, however some cyclic derivatives may be present. Although pyrophosphates and tripolyphosphate are technically polyphosphates, the polyphosphates desired are those having around four or more phosphate molecules so that surface adsorption at effective concentrations produces sufficient non-bound phosphate functions which enhance the anionic surface charge as well as hydrophilic character of the surfaces. The pyrophosphates are discussed separately under additional anticalculus agents. The inorganic polyphosphate salts desired include tetrapolyphosphate and hexametaphosphate, among others. Polyphosphates larger than tetrapolyphosphate usually occur as amorphous glassy materials. The present invention may use linear "glassy" polyphosphates having the formula:

wherein X is sodium or potassium and n averages from about 6 to about 125. Polyphosphates manufactured by FMC Corporation, Philadelphia, Pa., which are commercially known as Sodaphos (n≈6), Hexaphos (n≈13), and Glass H (n≈21) can be used. In certain embodiments the polyphosphate-Glass H can be used. These polyphosphates may be used alone or in a combination thereof.

The amount of the polymeric anti-tartar, anti-stain agent in certain embodiments may be from about 1% to about 35%, from about 2% to about 30%, from about 5% to about 25%, or from about 6% to about 20%, by weight of the total oral composition.

The compositions herein may contain from about 0.025% to about 9%, by weight of the composition, of a surfactant. The compositions may contain from about 0.5% to about 7%, alternatively from about 0.1% to about 5%, by weight of the composition, of the surfactant. In one embodiment, the surfactant is selected from nonionic surfactants, anionic surfactants, cationic surfactants, and mixtures thereof. In another embodiment, the surfactant is sodium lauryl sulfate.

In certain embodiments, the surfactant may be selected from anionic, nonionic, amphoteric, zwitterionic, cationic, or combinations thereof.

Examples of suitable surfactants for use herein include those that are reasonably stable and foam throughout a wide pH range. The surfactant may be anionic, nonionic, amphoteric, zwitterionic, cationic, or mixtures thereof. Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976.

Anionic surfactants useful herein include, for example, the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are examples of anionic surfactants of this type. Other suitable anionic surfactants include sarcosinates, such as sodium lauroyl sarcosinate, taurates, sodium lauryl sulfoacetate, sodium lauroyl isethionate, sodium laureth carboxylate, and sodium dodecyl benzenesulfonate. Combinations of anionic surfactants can also be employed. Many suitable anionic surfactants are disclosed by Agricola et al., U.S. Pat. No. 3,959,458.

Another class of anionic surfactants useful here are alkyl phosphates. The surface active organophosphate agents have a strong affinity for enamel surface and have sufficient surface binding propensity to desorb pellicle proteins and remain affixed to enamel surfaces. Suitable examples of organophosphate compounds include mono-, di- or triesters represented by the general structure below wherein Z1, Z2, or Z3 may be identical or different, at least one being an organic moiety, in one embodiment selected from linear or branched, alkyl or alkenyl group of from 1 to 22 carbon atoms, optionally substituted by one or more phosphate groups; alkoxylated alkyl or alkenyl, (poly)saccharide, polyol or polyether group.

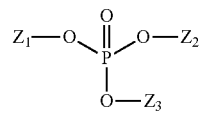

Some other agents include alkyl or alkenyl phosphate esters represented by the following structure:

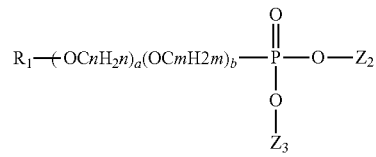

wherein R1 represents a linear or branched, alkyl or alkenyl group of from 6 to 22 carbon atoms, optionally substituted by one or more phosphate groups; n and m, are individually and separately, 2 to 4, and a and b, individually and separately, are 0 to 20; Z2 and Z3 may be identical or different, each represents hydrogen, alkali metal, ammonium, protonated alkyl amine or protonated functional alkyl amine such as an alkanolamine, or a R1-(OCnH2n)a(OCmH2m)b- group. Examples of suitable agents include alkyl and alkyl(poly)alkoxy phosphates such as lauryl phosphate; PPG5 ceteareth-10 phosphate; Laureth-1 phosphate; Laureth-3 phosphate; Laureth-9 phosphate; Trilaureth-4 phosphate; C12-18 PEG 9 phosphate; Sodium dilaureth-10 phosphate. In one embodiment, the alkyl phosphate is polymeric. Examples of polymeric alkyl phosphates include those containing repeating alkoxy groups as the polymeric portion, in particular 3 or more ethoxy, propoxy isopropoxy or butoxy groups.

Additional suitable polymeric organophosphate agents include dextran phosphate, polyglucoside phosphate, alkyl polyglucoside phosphate, polyglyceryl phosphate, alkyl polyglyceryl phosphate, polyether phosphates and alkoxylated polyol phosphates. Some specific examples are PEG phosphate, PPG phosphate, alkyl PPG phosphate, PEG/PPG phosphate, alkyl PEG/PPG phosphate, PEG/PPG/PEG phosphate, dipropylene glycol phosphate, PEG glyceryl phosphate, PBG (polybutylene glycol) phosphate, PEG cyclodextrin phosphate, PEG sorbitan phosphate, PEG alkyl sorbitan phosphate, and PEG methyl glucoside phosphate. Suitable non-polymeric phosphates include alkyl mono glyceride phosphate, alkyl sorbitan phosphate, alkyl methyl glucoside phosphate, alkyl sucrose phosphates.

Another suitable surfactant is one selected from sarcosinate surfactants, isethionate surfactants and taurate surfactants. In one embodiment, an alkali metal or ammonium salts of these surfactants are used. Examples of those sodium and potassium salts include following: lauroyl sarcosinate, myristoyl sarcosinate, palmitoyl sarcosinate, stearoyl sarcosinate and oleoyl sarcosinate, or combinations thereof. Of these anionic surfactants, examples of some which provide an unwanted taste within an oral care composition include, for example, SLS, lauroyl sarcosinate, and/or fatty alcohols or acids associated with natural based surfactants. The unwanted tastes often associated with these surfactants are soapy, chemical, and/or artificial.

The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Many of these suitable nonionic and amphoteric surfactants are disclosed by Gieske et al., U.S. Pat. No. 4,051,234, issued Sep. 27, 1977. Zwitterionic or amphoteric surfactants useful in oral care compositions include derivatives of aliphatic quaternary ammonium, phosphonium, and sulfonium compounds, in which the aliphatic radicals can be straight chain or branched, and one of the aliphatic substituents contains from about 8 to 18 carbon atoms and one contains an anionic water-solubilizing group, e.g., carboxy, sulfonate, sulfate, phosphate or phosphonate. Suitable betaine surfactants are disclosed in U.S. Pat. No. 5,180,577 to Polefka et al. Typical alkyl dimethyl betaines include decyl betaine or 2-(N-decyl-N,N-dimethylammonio) acetate, coco betaine or 2-(N-coco-N,N-dimethyl ammonio) acetate, myristyl betaine, palmityl betaine, lauryl betaine, cetyl betaine, cetyl betaine, stearyl betaine, etc. The amidobetaines are exemplified by cocoamidoethyl betaine, cocoamidopropyl betaine (CADB), and lauramidopropyl betaine. Of these surfactants, examples of some which provide an unwanted taste within an oral care composition include, for example, cocoamidopropyl betaine and lauryl betaine. The unwanted tastes often associated with these types of surfactants are soapy and chemical. These surfactants are generally included in an oral care composition in a range of about 0.5% to about 5%.

Cationic surfactants useful in the present invention include, for example, derivatives of quaternary ammonium compounds having one long alkyl chain containing from about 8 to 18 carbon atoms such as lauryl trimethylammonium chloride; cetyl pyridinium chloride; cetyl trimethylammonium bromide; coconut alkyltrimethylammonium nitrite; cetyl pyridinium fluoride or combinations thereof. Additional quaternary ammonium fluorides having detergent properties are described in U.S. Pat. No. 3,535,421 to Briner et al.

Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name PLURONIC), polyoxyethylene, polyoxyethylene sorbitan esters (sold under trade name TWEENS), Polyoxyl 40 hydrogenated castor oil, fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials.

The compositions herein may have a total solids content of 50% or less, by weight of the composition. In certain embodiments, the compositions may have total solids content of 40% or less. The total solid content includes the abrasives used herein.

The compositions herein may contain from about 5% to about 12%, by weight of the composition, of water. The amount of water refers to the total amount of free water available in the composition and may be added directly as water or may be added indirectly as a solvent or carrier for another material or naturally contained in the material.

The water activity value of the compositions of the present invention may be from about 0.25 to about 0.46 measured at about 22° C. As used herein, "water activity" refers to the equilibrium relative humidity or partial vapor pressure of the air above a product sample in a closed system divided by the relative humidity of air above pure water at the same temperature. Water activity can be expressed as % equilibrium relative humidity (% ERH) or $A_W$. % ERH=$100 \times A_W$. The compositions herein may have a water activity value of from about 0.25 to about 0.46.

Without being limited by theory, it is believed water activity is an important property of topical compositions such as oral care compositions including dentifrice. Water activity can affect ingredient solubility which in turn can be used to modify product rheology. Formulas that contain the same total concentration of water can have water activity values that differ dramatically depending on the hygroscopic characteristics of the other ingredients in the formula. Nearly all dentifrice paste or gel semi-solid formulations use polyhydric alcohols to help limit water loss over the self life of the product. Many polyhydric alcohols are classified as humectants and the most commonly used humectant materials in dentifrice formulations are glycerin, sorbitol, propylene glycol, polyethylene glycols and mixtures thereof. Other polyhydric alcohols can be used and frequently a blend of humectants is used to optimize cost, aesthetics, as well as, manufacturing requirements and other considerations.

Water activity may be measured using a ROTRONIC HYGROLAB 3, from Rotronic Instrument Corp., Hauppauge, N.Y., water activity instrument. Information is readily available from the manufacture as to the recommended calibration, sample preparation and other factors that need to be considered to assure measurement accuracy. An important variable to control in making a water activity measurement is temperature. Relative humidity or partial pressure of the water vapor is strongly dependent on temperature and therefore accuracy of the temperature control and measurement is an important component in reporting water activity data.

Further, without being limited by theory, in addition to humectants and water, other materials can affect the water activity of a composition. Other materials that may affect the water activity value include salts. However, generally varying the level of humectants is more efficient and practical for topical formulations. Each humectant has an individual capacity to affect water activity with glycerin being the most effective. By combining humectants and adjusting the free water added to a formulation the same water activity value can be achieved using a variety of different formulas. Although modeling can be done to develop the relationship of water activity to a particular formulation design space, direct measurement using a water activity meter is often more practical since the measurement can be done in a matter of minutes using any of the various water activity meters commercially available.

The compositions herein may contain at least 0.25%, by weight of the composition, of an oral care component.

In one embodiment, the oral care component is selected from stannous chloride, triclosan, zinc lactate, zinc oxide, zinc citrate, and mixtures thereof. In one embodiment, the composition contains from about 0.25% to about 3% stannous chloride. In one embodiment, the oral care component is zinc citrate.

In one embodiment, the oral care compositions contain from about 0.25% to about 8%, by weight of the composition of at least one oral care component selected from metal salts, antimicrobial agents, bad breath reduction agents, bleaching agents, or a combination thereof. In one embodiment, the oral care composition comprises from about 0.025% to about 7%, alternatively from about 0.25% to about 5%, by weight of the composition, of the oral care component.

The compositions may further include additional oral care component, discussed below as "optional oral care components". Such oral care components are generally present in an amount of about 0.0001% to about 8%, by weight of the composition.

Metal salts have a wide range of functions from antimicrobial agents to sensitivity agents and/or buffers. In one embodiment, the metal salt comprises a zinc salt, stannous salt, potassium salt, copper salt, or a combination thereof.

In one embodiment, the zinc salt is selected from zinc fluoride, zinc chloride, zinc iodide, zinc chlorofluoride, zinc acetate, zinc hexafluorozirconate, zinc sulfate, zinc lactate, zinc tartrate, zinc gluconate, zinc citrate, zinc malate, zinc glycinate, zinc pyrophosphate, zinc metaphosphate, zinc oxalate, zinc phosphate, zinc carbonate, and combinations thereof. In another embodiment, the zinc salt is selected from zinc chloride, zinc citrate, zinc gluconate, zinc lactate, zinc oxide, and combinations thereof.

In one embodiment, the potassium salt is selected from potassium nitrate, potassium citrate, potassium oxalate, potassium bicarbonate, potassium acetate, potassium chloride, and combinations thereof.

In one embodiment, the copper salt is selected from copper fluoride, copper chloride, copper iodide, copper chlorofluoride, copper acetate, copper hexafluorozirconate, copper sulfate, copper lactate, copper tartrate, copper gluconate, copper citrate, copper malate, copper glycinate, copper pyrophosphate, copper metaphosphate, copper oxalate, copper phosphate, copper carbonate, and combinations thereof. In a further embodiment, the copper salt is selected from copper gluconate, copper acetate, copper glycinate, and combinations thereof.

In another embodiment, the stannous salt is selected from stannous fluoride, stannous chloride, stannous iodide, stannous chlorofluoride, stannous acetate, stannous hexafluorozirconate, stannous sulfate, stannous lactate, stannous tartrate, stannous gluconate, stannous citrate, stannous malate, stannous glycinate, stannous pyrophosphate, stannous metaphosphate, stannous oxalate, stannous phosphate, stannous carbonate, and combinations thereof. In a further embodiment, the stannous salt is selected from stannous fluoride, stannous chloride, stannous chloride dihydrate, stannous fluoride, stannous lactate, stannous gluconate, stannous sulfate, and combinations thereof.

Dentifrices containing stannous salts, particularly stannous fluoride and stannous chloride, are described in U.S. Pat. No. 5,004,597 to Majeti et al. Other descriptions of stannous salts are found in U.S. Pat. No. 5,578,293 issued to Prencipe et al. and in U.S. Pat. No. 5,281,410 issued to Lukacovic et al. In addition to the stannous ion source, other ingredients needed to stabilize the stannous may be included, such as the ingredients described in Majeti et al. and Prencipe et al.

One example of an antimicrobial agent useful herein is a quaternary ammonium compound. Those useful herein include, for example, those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl)ammonium bromide, benzyl dimethoylstearyl ammonium chloride, cetylpyridinium chloride, quaternized 5-amino-1,3-bis(2-ethylhexyl)-5-methyl hexahydropyrimidine, benzalkonium chloride, benzethonium chloride and methyl benzethonium chloride are exemplary of typical quaternary ammonium antibacterial agents.

Other compounds include bis[4-(R-amino)-1-pyridinium] alkanes as disclosed in U.S. Pat. No. 4,206,215, Jun. 3, 1980, to Bailey. Other quaternary ammonium compounds include the pyridinium compounds. Examples of pyridinium quaternary ammonium compounds include cetylpyridinium and tetradecylpyridinium halide salts (i.e., chloride, bromide, fluoride and iodide).

The oral care compositions of the present invention may also include other antimicrobial agents including non-cationic antimicrobial agents such as halogenated diphenyl ethers, phenolic compounds including phenol and its homologs, mono and poly-alkyl and aromatic halophenols, resorcinol and its derivatives, xylitol, bisphenolic compounds and halogenated salicylanilides, benzoic esters, and halogenated carbanilides. Also useful antimicrobials are enzymes, including endoglycosidase, papain, dextranase, mutanase, and combinations thereof. Such agents are disclosed in U.S. Pat. No. 2,946,725, Jul. 26, 1960, to Norris et al. and in U.S. Pat. No. 4,051,234 to Gieske et al. Examples of other antimicrobial agents include chlorhexidine, triclosan, triclosan monophosphate, and flavor oils such as thymol. Triclosan and other agents of this type are disclosed in Parran, Jr. et al., U.S. Pat. No. 5,015,466, and U.S. Pat. No. 4,894,220 to Nabi et al.

The compositions of the present invention may contain from about 0.01% to about 4.0%, by weight of the composition, of an oral care component selected from bad breath reduction agents. These agents generally work to reduce breath malodor.

Examples of bad breath reduction agents include copper salts and carbonyl compounds such as ascorbic acid [3-oxo-L-gulofuranolactone]; cis-jasmone[3-methyl-2-(2-pentenyl)-2-cyclopentenone]; 2,5-dimethyl-4-hydroxy-3(2H)-furanone; 5-ethyl-3-hydroxy-4-methyl-2(5H)-furanone; vanillin [4-hydroxy-3-methoxybenzaldehyde]; ethyl vanillin; anisaldehyde[4-methoxybenzaldehyde]; 3,4-methylenedioxybenzaldehyde; 3,4-dimethoxybenzaldehyde; 4-hydroxybenzaldehyde; 2-methoxybenzaldehyde; benzaldehyde; cinnamaldehyde[3-phenyl-2-propenal]; hexyl cinnamaldehyde; α-methyl cinnamaldehyde; ortho-methoxy cinnamaldehyde; citral; linalool; geraniol; eugenol; or combinations thereof.

The compositions of the present invention may contain from about 0.01% to about 30%, from about 0.1% to about 10%, or from about 0.5% to about 5%, by weight of the composition, of an oral care component selected from bleaching agents. Bleaching agents are generally agents which whiten teeth.

Examples of bleaching agents include peroxides, perborates, percarbonates, peroxyacids, persulfates, and combinations thereof. Suitable peroxide compounds include hydrogen peroxide, urea peroxide, calcium peroxide, sodium peroxide, zinc peroxide, or combinations thereof. One example of a percarbonate is sodium percarbonate. An example of a persulfate includes oxones.

The compositions of the present invention may also contain from about 0.0001% to about 8% or from about 0.001% to about 5%, by weight of the composition, of an optional oral care component. Optional oral care components include flavors, anti-tartar agents, colorants, sensates, sweeteners, anti-calculus agents, anti-staining agents and combinations thereof.

In one embodiment, the composition further includes a flavoring agent, or mixtures thereof. Examples of some flavoring agents useful herein include mint oils, wintergreen, clove bud oil, cassia, sage, parsley oil, marjoram, lemon, orange, propenyl guaethol, heliotropine, 4-cis-heptenal, diacetyl, methyl-ρ-tert-butyl phenyl acetate, methyl salicylate, ethyl salicylate, 1-menthyl acetate, oxanone, α-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, α-terpineol, linalool, limonene, citral, neral, geranial, geraniol nerol, maltol, ethyl maltol, anethole, dihydroanethole, carvone, menthone, β-damascenone, ionone, γ-decalactone, γ-nonalactone, γ-undecalactone, or combinations thereof. In one embodiment, the flavoring agent is selected from oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof.

One example of an antitartar agent is a pyrophosphate salt as a source of pyrophosphate ion. The pyrophosphate salts useful in the present compositions include, for example, the mono-, di- and tetraalkali metal pyrophosphate salts and combinations thereof. Disodium dihydrogen pyrophosphate ($Na_2H_2P_2O_7$), sodium acid pyrophosphate, tetrasodium pyrophosphate ($Na_4P_2O_7$), and tetrapotassium pyrophosphate ($K_4P_2O_7$) in their unhydrated as well as hydrated forms are further species.

The compositions herein may include a coloring agent. The coloring agent may be in the form of an aqueous solution, preferably 1% coloring agent in a solution of water. In one embodiment, the composition contains from about 0.01% to about 5%, by weight of the coloring solution.

Examples of coloring agents useful herein include D&C Yellow No. 10, FD&C Blue No. 1, FD&C Red No. 40, D&C Red No. 33 and combinations thereof. In one embodiment, the composition comprises from about 0.0001% to about 0.1%, alternatively from about 0.001% to about 0.01%, by weight of the oral care composition, of a colorant.

Sensate molecules such as cooling, warming, and tingling agents are useful to deliver signals to the consumer. The most well-known cooling sensate compound is menthol, particularly 1-menthol, which is found naturally in peppermint oil. Other isomers of menthol (neomenthol, isomenthol and neoisomenthol) have somewhat similar, but not identical odor and taste, i.e., having disagreeable notes described as earthy, camphor, musty, etc.

Among synthetic coolants, many are derivatives of or are structurally related to menthol, i.e., containing the cyclohexane moiety, and derivatized with functional groups including carboxamide, ketal, ester, ether and alcohol. Examples include the ρ-menthanecarboxamide compounds such as N-ethyl-ρ-menthan-3-carboxamide, known commercially as "WS-3", and others in the series such as WS-5 (N-ethoxycarbonylmethyl-ρ-menthan-3-carboxamide), WS-12 [N-(4-methoxyphenyl)-ρ-menthan-3-carboxamide] and WS-14 (N-tert-butyl-ρ-menthan-3-carboxamide). Examples of menthane carboxy esters include WS-4 and WS-30. An example of a synthetic carboxamide coolant that is structurally unrelated to menthol is N,2,3-trimethyl-2-isopropylbutanamide, known as "WS-23". Additional examples of synthetic coolants include alcohol derivatives such as 3-(1-menthoxy)-propane-1,2-diol known as TK-10, isopulegol (under the tradename Coolact P) and ρ-menthane-3,8-diol (under the tradename Coolact 38D) all available from Takasago; menthone glycerol acetal known as MGA; menthyl esters such as menthyl acetate, menthyl acetoacetate, menthyl lactate known as Frescolat® supplied by Haarmann and Reimer, and monomenthyl succinate under the tradename Physcool from V. Mane. TK-10 is described in U.S. Pat. No. 4,459,425 to Amano et al. Other alcohol and ether derivatives of menthol are described e.g., in GB 1,315,626 and in U.S. Pat. Nos. 4,029,759; 5,608,119; and 6,956,139. WS-3 and other carboxamide cooling agents are described for example in U.S. Pat. Nos. 4,136,163; 4,150,052; 4,153,679; 4,157,384; 4,178,459 and 4,230,688. Additional N-substituted ρ-menthane carboxamides are described in WO 2005/049553A1 including N-(4-cyanomethylphenyl)-ρ-menthanecarboxamide, N-(4-sulfamoylphenyl)-ρ-menthanecarboxamide, N-(4-cyanophenyl)p-menthanecarboxamide, N-(4-acetylphenyl)-ρ-menthanecarboxamide, N-(4-hydroxymethylphenyl)-ρ-menthanecarboxamide and N-(3-hydroxy-4-methoxyphenyl)-ρ-menthanecarboxamide. Other N-substituted ρ-menthane carboxamides include amino acid derivatives such as those disclosed in WO 2006/103401 and in U.S. Pat. Nos. 4,136,163; 4,178,459 and 7,189,760 such as N-((5-methyl-2-(1-methylethyl)cyclohexyl)carbonyl)glycine ethyl ester and N-((5-methyl-2-(1-methylethyl)cyclohexyl)carbonyl)alanine ethyl ester. Menthyl esters including those of amino acids such as glycine and alanine are disclosed e.g., in EP 310,299 and in U.S. Pat. Nos. 3,111,127; 3,917,613; 3,991,178; 5,703,123; 5,725,865; 5,843,466; 6,365,215;

6,451,844; and 6,884,903. Ketal derivatives are described, e.g., in U.S. Pat. Nos. 5,266,592; 5,977,166 and 5,451,404. Additional agents that are structurally unrelated to menthol but have been reported to have a similar physiological cooling effect include alpha-keto enamine derivatives described in U.S. Pat. No. 6,592,884 including 3-methyl-2-(1-pyrrolidinyl)-2-cyclopenten-1-one (3-MPC), 5-methyl-2-(1-pyrrolidinyl)-2-cyclopenten-1-one (5-MPC), and 2,5-dimethyl-4-(1-pyrrolidinyl)-3(2H)-furanone (DMPF); icilin (also known as AG-3-5, chemical name 1-[2-hydroxyphenyl]-4-[2-nitrophenyl]-1,2,3,6-tetrahydropyrimidine-2-one) described in Wei et al., J. Pharm. Pharmacol. (1983), 35:110-112.

Some examples of warming sensates include ethanol; capsicum; nicotinate esters, such as benzyl nicotinate; polyhydric alcohols; capsicum powder; a capsicum tincture; capsicum extract; capsaicin; homocapsaicin; homodihydrocapsaicin; nonanoyl vanillyl amide; nonanoic acid vanillyl ether; vanillyl alcohol alkyl ether derivatives such as vanillyl ethyl ether, vanillyl butyl ether, vanillyl pentyl ether, and vanillyl hexyl ether; isovanillyl alcohol alkyl ethers; ethylvanillyl alcohol alkyl ethers; veratryl alcohol derivatives; substituted benzyl alcohol derivatives; substituted benzyl alcohol alkyl ethers; vanillin propylene glycol acetal; ethylvanillin propylene glycol acetal; ginger extract; ginger oil; gingerol; zingerone; or combinations thereof.

Sweetening agents can be added to the compositions. Examples of sweetening agents useful herein include saccharin, dextrose, sucrose, lactose, xylitol, maltose, levulose, aspartame, sodium cyclamate, D-tryptophan, dihydrochalcones, acesulfame, and mixtures thereof. In one embodiment, the composition contains from about 0.005% to about 5%, by weight of the composition, of a sweetening agent Examples of sweetening agents useful herein include those selected from saccharin, chloro-sucrose (sucralose), steviolglycosides, rebaudioside A, rebaudioside B, rebaudioside C, rebaudioside D, rebaudioside E, rebaudioside F, dulcoside A, dulcoside B, rubusoside, stevia, stevioside, acesulfame K, xylitol, neohesperidine DC, alitame, aspartame, neotame, alitame, thaumatin, cyclamate, glycyrrhizin, mogroside IV, mogroside V, Luo Han Guo sweetener, siamenoside, monatin and its salts (monatin SS, RR, RS, SR), curculin, monellin, mabinlin, brazzein, hemandulcin, phyllodulcin, glycyphyllin, phloridzin, trilobtain, baiyanoside, osladin, polypodoside A, pterocaryoside A, pterocaryoside B, mukurozioside, phlomisoside I, periandrin I, abrusoside A, cyclocarioside I,N—[N-[3-(3-hydroxy-4-methoxyphenyl)propyl]-L-α-aspartyl]-L-phenylalanine 1-methyl ester, N—[N-[3-(3-hydroxy-4-methoxyphenyl)-3-methylbutyl]-L-α-aspartyl]-L-phenylalanine 1-methyl ester, N—[N-[3-(3-methoxy-4-hydroxyphenyl)propyl]-L-α-aspartyl]-L-phenylalanine 1-methyl ester, salts thereof, and combinations thereof.

In one embodiment, the sweetening agent is selected from, REBIANA, NHDC, acesulfame K, and combinations thereof. Additionally, a flavor enhancer such as glucono-δ-lactone can be added to the composition.

Anticalculus agents useful herein include materials known to be effective in reducing calcium phosphate mineral deposition related to calculus formation. Examples include pyrophosphates, tripolyphosphates, synthetic anionic polymers [including polyacrylates and copolymers of maleic anhydride or acid and methyl vinyl ether (e.g., Gantrez), as described, for example, in U.S. Pat. No. 4,627,977 to Gaffar et al.; as well as, e.g., polyamino propane sulfonic acid (AMPS)], zinc citrate trihydrate, diphosphonates (e.g., EHDP; AHP), polypeptides (such as polyaspartic and polyglutamic acids), and mixtures thereof.

The compositions herein may include a stain-reducing agent. Such stain-reducing agent may be particularly desirable for compositions that contain stannous ions. Examples of stain-reducing agents useful herein include PLASDONE S-630 (Ashland Specialty Ingredients, Wayne, N.J.) or aluminum hydrate may further be added to the composition. PLASDONE is polyvinyl pyrrolidone (PVP) that can be synthesized by polymerizing vinylpyrrolidone. Commercially, it has been produced as a series of products having mean molecular weights ranging from 10,000 to 700,000. Herein, the low molecular weights and middle molecular weights (from about 10,000 to about 100,000) are preferred. In order to remove stain effectively, the level of PVP is preferably from about 0.5% to about 10%, more preferably from about 1.0% to about 7.0%, and even more preferably from about 1.5% to about 5.0%.

The compositions herein typically have a pH of from about 4 to about 10. In one embodiment, the pH is from about 4.5 to about 9, alternatively from about 5.5 to about 7. In one embodiment, the pH of the composition is measured within one hour of the final product being formed. In another embodiment, the pH of the composition is the neat pH, before packaging.

The compositions herein may include a pH modifier to obtain the desirable pH.

In certain embodiments, the composition further contains less than about 1%, by weight of the composition, of clay particles.

The compositions of the present invention may contain titanium dioxide. Titanium dioxide is a white powder which adds opacity to the compositions. In certain embodiments, the composition contains titanium dioxide from about 0.25% to about 5%, from about 0.25% to about 2.5%, or from about 0.25% to 1.5%, by weight of the composition.

Examples 1A-1D

Dentifrice Compositions

Dentifrice compositions according to the present invention are shown in Examples 1A, 1B, 1C, and 1D, below alongside a comparative formulation. All of the dentifrice formulations are made by traditional means and processes. Compositions 1A-1D exhibit improved rheology and stand-up versus the comparative example.

| INGREDIENT | Comparative Formula | 1A | 1B | 1C | 1D |
|---|---|---|---|---|---|
| Glycerin | 34 | 31 | 44 | 32.25 | 29 |
| Water | | 2.9 | 0.23 | 1.016 | 7.49 |
| Propylene Glycol | 10.0 | 6.5 | 6.0 | 8.0 | 7.5 |
| PEG 6 | 6.0 | 7.0 | | 7.0 | |
| PEG 12 | | | | | 6.0 |
| PEG 4000 | | 2.1 | 1.0 | 0.5 | 3.8 |
| PLURIOL E 4000 Pastille* | | | | | |
| PEG 8000 | | 2.0 | | | |
| PLURIOL E 8000 NF Prill* | | | | | |
| Stannous Fluoride | 0.45 | 0.45 | 0.45 | 0.45 | 0.45 |
| Zinc Lactate | 2.0 | 1.5 | 2.3 | 2.7 | 3.0 |
| Sodium Gluconate | 0.5 | 1.0 | 0.75 | 0.50 | 0.66 |
| Sodium Saccharin | 0.5 | 0.25 | 0.4 | 0.5 | 0.4 |
| Trisodium Phosphate | 1.25 | 1.0 | 1.0 | 1.1 | 1.0 |
| Sodium Polyphosphate Particles | 15.0 | 13.0 | 12.5 | 14.0 | 13.0 |

-continued

| INGREDIENT | Comparative Formula | 1A | 1B | 1C | 1D |
|---|---|---|---|---|---|
| Precipitated Silica ZEODENT 119** | 24.0 | 13.0 | 13.0 | 15.0 | 12.5 |
| Precipitated Silica ZEODENT 109** | | 13.0 | 12.0 | 10.0 | 12.5 |
| Precipitated Silica ZEODENT 165** | | | | | 1.0 |
| Carrageenan | 0.6 | 0.15 | 0.30 | 0.40 | .22 |
| Hydroxyethyl Cellulose | | | | .30 | |
| Xanthan Gum | 0.30 | 0.1 | 0.12 | 0.2 | 0.08 |
| Titanium Dioxide | | | | 1.0 | 0.1 |
| Sodium Lauryl Sulfate Solution (27.9%) | 3.5 | 3.0 | 4.0 | 3.0 | |
| Poloxamer 407 | | | | 0.5 | 1.0 |
| Flavor | 1.3 | 1.25 | 1.15 | 1.0 | 1.0 |
| Color Solution | 0.300 | 0.300 | 0.300 | 0.084 | |
| Polyethylene microwhite specks | 0.3 | 0.5 | | | 0.3 |
| TOTAL | 100 | 100 | 100 | 100 | 100 |

*PEG 4000 PLURIOL E 4000 Pastille and PEG 8000 PLURIOL E 8000 NF Prill are polyethylene glycol materials having an average molecular weight of 4000 and 8000, respectively and are commercially available from BASF (Florham Park, New Jersey, USA.
**Precipitated Silicas ZEODENT 119, ZEODENT 109 and ZEODENT 165 are all precipitated silicas commercially available from Huber (Havre de Grace, Maryland, USA).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Except as otherwise noted, the articles "a", "an", and "the" mean "one or more".

As used herein, "contain" or "comprising" means that other steps and other ingredients which do not affect the end result can be added. This term encompasses the terms "consisting of" and "consisting essentially of". The compositions and methods/processes of the present invention can contain, include, comprise, consist of, and consist essentially of the elements and limitations of the invention described herein, as well as any of the additional or optional ingredients, components, steps, or limitations described herein.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care composition comprising:
   a) a humectant component from about 10% to about 77%, by weight of the composition, wherein the humectant component comprises:
      i) from about 0.25% to about 7%, by weight of the composition, of a structuring humectant selected from polyethylene glycols having an average molecular weight of from about 3,000 to about 8,000, and mixtures thereof; and
      ii) at least one secondary humectant;
         wherein the secondary humectant comprises glycerin from 29% to 44%, by weight of the composition:
   b) a precipitated silica from about 5% to about 35%, weight of the composition;
   c) from about 0% to about 1.5%, by weight of the composition, of a viscosity modifier selected from the group consisting of gums, binders, cellulosic thickeners, and mixtures thereof;
   d) a total solids content of 50% or less, by weight of the composition;
   e) a water content from about 5% to about 12%, by weight of the composition;
   and wherein the composition comprises a water activity value from about 0.25 to about 0.46 measured at about 22° C.

2. The oral care composition according to claim 1, wherein the precipitated silica has an oil absorption of less than about 250 cc/100 g, a BET surface area of less than about 150 m2/g, and a median particle size of less than about 0.50 microns.

3. The oral care composition according to claim 1, wherein the composition comprises less than about 5% silica gels, by weight of the composition.

4. The oral care composition according to claim 1, wherein the composition comprises less than about 5% of a thickening silica, by weight of the composition.

5. The oral care composition according to claim 1, further comprising fluoride from about 50 ppm to about 3500 ppm, wherein the fluoride is selected from the group consisting of stannous fluoride, sodium fluoride, sodium monofluorophosphate, and mixtures thereof.

6. The oral care composition according to claim 1, wherein the structuring humectant is selected from polyethylene glycols having an average molecular weight of from about 3,000 to about 6,000.

7. The oral care composition according to claim 1, wherein the structuring humectant is selected from polyethylene glycols having an average molecular weight of from about 3,500 to about 5,500.

8. The oral care composition according to claim 1, wherein the composition comprises the structuring humectant from about 1% to about 4%, by weight of the composition.

9. The oral care composition according to claim 1, wherein the composition further comprises at least 0.25%, by weight of the composition, of an oral care component selected from the group consisting of stannous chloride, peroxide, triclosan, zinc lactate, zinc oxide, zinc citrate, sodium polyphosphate, and mixtures thereof.

10. An oral care composition comprising:
    a) a humectant component from about 40% to about 77%, by weight of the composition, wherein the humectant component comprises:
       i) a structuring humectant from about 0.25% to about 7%, by weight of the composition, selected from polyethylene glycols having an average molecular weight of from about 3,000 to about 8,000, and mixtures thereof; and ii) at least one secondary humectant;
wherein the secondary humectant comprises glycerin from 29% to 44%, by weight of the composition;
b) a fluoride from about 50 ppm to about 3500 ppm;
c) from about 0% to about 1.5%, by weight of the composition, of a viscosity modifier selected from the group consisting of gums, binders, cellulosic thickeners, and mixtures thereof;
d) from about 5% to about 35%, by weight of the composition, of a precipitated silica;
e) a surfactant from about 0.025% to about 9% by weight of the composition; and
f) a water content from about 5% to about 12%, by weight of the composition;
wherein the composition comprises a water activity value of front about 0.25 to about 0.46 measured at about 22° C.;
and wherein the structuring humectant forms a crystalline structure.

11. An oral care composition according to claim 10, wherein the fluoride is selected from the group consisting of stannous fluoride, sodium fluoride, sodium monofluorophosphate, and mixtures thereof.

12. An oral care composition according to claim 10, wherein the surfactant is selected from the group consisting of nonionic surfactants, anionic surfactants, cationic surfactants, and mixtures thereof.

13. An oral care composition according to claim 10, wherein the composition comprises less than 2.5% titanium dioxide, by weight of the composition.

14. An oral care composition according to claim 10, wherein the composition has a pH of front about 5.0 to about 6.5.

15. An oral care composition according to claim 10, wherein the composition further comprises a flavoring agent.

16. An oral care composition according to claim 10, wherein the composition comprises less than about 1% clay particles, by weight of the composition.

17. The oral care composition according to claim 1, wherein the structuring humectant forms a crystalline structure.

* * * * *